United States Patent [19]

Hashizume et al.

[11] Patent Number: 5,094,942

[45] Date of Patent: Mar. 10, 1992

[54] DETECTION OF ANTIBODIES BINDING CARBOXYPEPTIDASE IN SERUM OF CANCER PATIENTS

[75] Inventors: Shuichi Hashizume; Katsumi Mochizuki, both of Yokohama, Japan

[73] Assignee: Morinaga & Co., Ltd., Tokyo, Japan

[21] Appl. No.: 347,638

[22] Filed: May 5, 1989

[30] Foreign Application Priority Data

May 13, 1988 [JP] Japan ............................. 63-116289
Jan. 18, 1989 [JP] Japan ............................. 1-9254

[51] Int. Cl.⁵ .................. G01N 33/574; G01N 33/53; G01N 33/543
[52] U.S. Cl. .................... 435/7.23; 435/7.9; 436/513; 436/518; 436/548; 436/813
[58] Field of Search ............ 435/7.1, 723, 7.9, 7.4, 435/172.2, 240.27; 436/501, 536, 543, 548, 64, 813, 819, 513, 518; 530/387, 808, 828; 935/110

[56] References Cited

U.S. PATENT DOCUMENTS 4,732,862 3/1988 Bartorelli et al. .................. 436/513

OTHER PUBLICATIONS

*Journal of Surgical Oncology*, vol. 39, pp. 108-113 (1988).
*In Vitro Cellular & Developmental Biology*, vol. 21, No. 10, pp. 593-596 (1985).
*Chemical Abstracts*, vol. 103, No. 7, pp. 400, resume No. 520434f (1985).

*Primary Examiner*—Esther L. Kepplinger
*Assistant Examiner*—Donna C. Wortman
*Attorney, Agent, or Firm*—Nixon & Vanderhye

[57] ABSTRACT

The present invention provides a serodiagnosis method for the detection of cancers, which comprises employing an antigen recognizable by a human monoclonal antibody and derived from animals other than human.

14 Claims, 1 Drawing Sheet

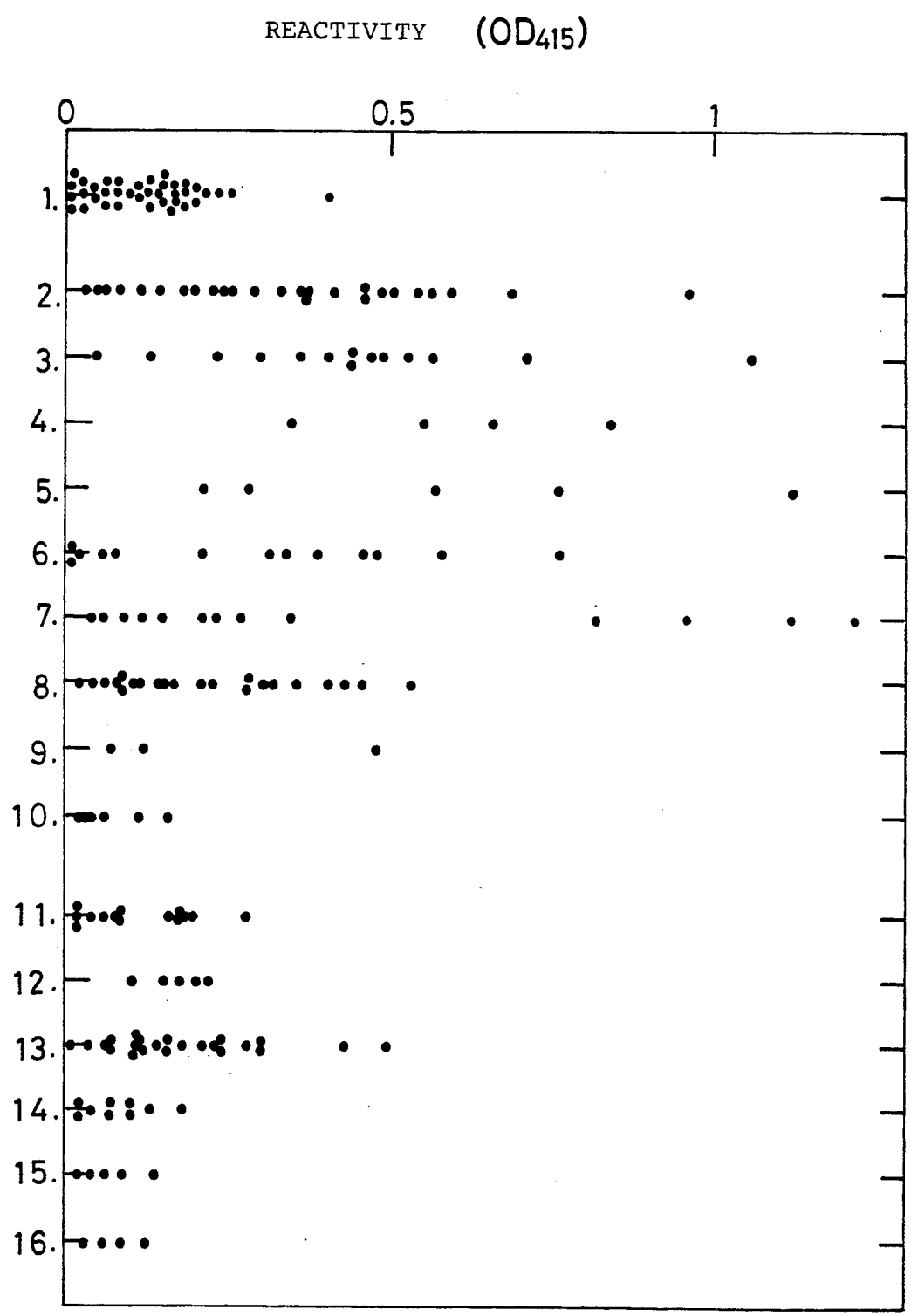

DETECTION OF ANTIBODIES BINDING CARBOXYPEPTIDASE IN SERUM OF CANCER PATIENTS

BACKGROUND OF THE INVENTION

1. Field of the Invention

The present invention relates to a serodiagnosis method for the detection of cancers, which comprises using an antigen recognizable by a human monoclonal antibody, particularly, the antigen derived from animals other than human.

2. The Prior Art

In these days, various reports have been published relating to a method for the preparation of human monoclonal antibodies which may react with cancer cells, which comprises culturing human-human hybridomas obtained by the fusion of antibody-producing cells from cancer patients with partner cells such as myeloma cells (Proc. Nat. Acad. Sci., U.S.A., 77, 6841 (1980); Brit. J. Cancer, 43, 105 and 696 (1981); Lancet, i 11 (1982); Eur. J. Cancer, 19, 347 (1983); J. Exp. Med., 159, 537 (1984); Cancer Res., 45, 263 and 3951 (1985); J. Immunol., 137, 1083 (1986)).

The human monoclonal antibodies described in these reports are not specific to cancer cells and may therefore react with normal cells as well. Furthermore, as antigens recognized by said monoclonal antibodies, substantially only ganglioside GM3 or GD3 which may be recognized by a human monoclonal antibody produced by a hybridoma has been known up to now (Proc. Nat. Acad. Sci., U.S.A., 84, 2416 (1987)). It thus appears that a serodiagnosis method for the detection of cancers, which comprises using an antigen recognizable by a human monoclonal antibody has not yet been disclosed till now. Similarly, there has been published up to now no serodiagnosis method for the detection of cancers, which comprises using an antigen recognizable by a human monoclonal antibody and derived from animals other than human.

Tumor markers conventionally used in an assay method for cancer such as a serodiagnosis one are derived from human. Such tumor markers may include embryonic proteins such as alpha-fetoprotein and carcinoembryonic antigen, blood group substances, hormones and isoenzymes. The assay method using such tumor markers can advantageously treat many samples in a simple manner and have been more important not only for screening cancers but also for monitoring therapeutic and postoperative effects.

However, the assay method using the above tumor markers or antigens conventionally known may not sufficiently detect cancers. In addition, it is very difficult to obtain the markers or antigens in a large amount, since they have their origin in human. Furthermore, since such antigens or markers may disadvantageously exist also in healthy individuals, their use would increase a ratio of false positives in the assay method. On the other hand, it is very difficult to diagnose cancers in their early stage by conventional assay methods which detect an amount of the tumor markers or antigens in blood because only a small amount thereof is present in that stage.

SUMMARY OF THE INVENTION

Antigenic materials which may be derived from animals other than human and advantageously used in a serodiagnosis method for cancers were surveyed, and the present inventors have found that the animal-derived antigenic materials which may be recognized by a human monoclonal antibody produced by a human-human hybridoma originated from antibody-producing cells of cancer patients, especially by a human monoclonal antibody produced by HB4C5, may function as the above antigen The present invention has been completed on the basis of these findings.

An object of the present invention, therefore, is to provide a serodiagnosis method for the detection of cancers, which comprises using an antigen recognizable by a human monoclonal antibody, particularly, the antigen derived from animals other than human.

The present invention is characterized in that an amount of antibodies against cancer-associated antigens in blood as described above is determined instead of that of the antigens themselves, which have been determined in the conventional methods. Accordingly, even in the case that only an extremely small amount of the antigens is present in blood, it is still possible to determine the amount of the antibodies, because they may have been increased in human body. Thus, the present invention may provide the possibility of an early diagnosis of cancers.

DETAILED DESCRIPTION OF THE INVENTION (1) Preparation of cells producing a human monoclonal antibody:

Lymphocytes ($2 \times 10^7$ cells) obtained from the lymph node or peripheral blood of patients with lung cancer are fused with a parent cell line suitable for the preparation of a human-human hybridoma, NAT-30 (In Vitro Cell. Develop. Biol., 21, 593 (1985)) or HO-323 (Cell Biol. Intern. Reports, 10, 77 (1986)) in the presence of polyethyleneglycol (M.W.=4,000 or 1,500) in a conventional manner to prepare hybridomas. From the resultant hybridomas, hybridomas which may produce human monoclonal antibodies reactive with the lung cancer cell line PC-8 but not with normal cell lines are selected.

An example of the hybridoma producing the above cancer-specific human monoclonal antibody is HB4C5 (In Vitro Cell. Develop. Biol., 21, 593 (1985)), which was deposited on May 12, 1988 at the Fermentation Research Institute, Agency of Industrial Science and Technology (JAPAN) and designated the accession number FERM BP-1879. This deposit was made pursuant to the Budapest Treaty On the International Recognition of the Deposit of Microorganism for the Purpose of Patent Procedure.

(2) Research for the antigenic materials:

The research for the occurrence of the antigenic materials which may be recognized by the human monoclonal antibody of class IgM produced by the human-human hybridoma HB4C5 is made among animals such as swine, bovine and mouse, revealing the fact that such material is present in a large amount in pancreas of these animals.

On the above research, reactivity of antigenic materials in various samples with the human monoclonal antibody according to the present invention is determined in the following procedure. Determination procedure:

An extract of the pancreas as well as samples obtained in each purification step are resolved by sodium dodecyl sulfate (SDS) polyacrylamide gel electrophoresis (SDS-PAGE) on continuous (4–20%) gradient gel (Laemmli, et al., Nature, 227, 680 (1970)). The resolved proteins are electrophoretically transferred to a nitrocellulose membrane, and the proteins thus transferred on the membrane are reacted with the human monoclonal antibody according to the present invention by the following immunostaining method:

All the treatments in the following procedure are performed at room temperature. Prior to immune reaction, the nitrocellulose membrane is blocked by being soaked in phosphate buffered saline (PBS) containing 0.05% Tween 20 (PBS/Tween) for 1 hour in order to avoid non-specific adsorption. After the blocking, the membrane is treated with the human monoclonal antibody for 1 hour, washed with PBS/Tween for 30 minutes and reacted with a peroxidase-conjugated anti-human IgM antibody for 1 hour. After washing with PBS/Tween, the membrane is incubated in a substrate DAB (3,3'-diaminobenzidine tetra hydrochloric acid) solution for 15 minutes, so that the antigenic materials bound with the human monoclonal antibody are stained in brown.

These antigenic materials recognized by the human monoclonal antibody according to the present invention have been identified carboxypeptidases as described in EXAMPLEs.

Carboxypeptidases may be obtained from pancreas of bovine (Methods Enzymol., 19, 460 (1970)) or from pancreatic juice of rat (Anal. Biochem., 171, 294 (1988)). Alternatively, carboxypeptidases may be purified by the method described in Example 1 infra.

(3) Serodiagnosis method:

The antigen recognized by the human monoclonal antibody according to the present invention is diluted by the addition of sodium carbonate buffer (pH 9.5) to a final concentration of 10 μg/ml. To 48 wells of a 96-well immunoplate is added an 100 μl portion of the diluted antigen and incubated for 1 hour at 37° C. to coat each well with the added antigen. To the rest of the wells is added the sodium carbonate buffer without the antigen and treated in the same manner as described above, which will serve as control wells. The plate is washed twice with PBS and incubated for blocking with 10% fetal calf serum (FCS)/PBS for 1 hour at 37° C. After discarding the blocking solution a 50 μl of each serum sample diluted 1:200 with 10% FCS/PBS is immediately added to the antigen-coated and control wells treated above and incubated for 1 hour at 37° C. In case that an antibody which may react with the coated antigen is contained in the serum sample, the antibody may bind to the antigen and be accordingly immobilized on the plate. The plate is washed three times with PBS/Tween, followed by the determination of an amount of the immobilized antibody by an usual method. An 100 μl of peroxidase-conjugated anti-human IgG or IgM is added to each well and incubated for 30 minutes at 37° C. After washing three times L with PBS/Tween, a 100 μl of widely-used substrate solution containing 2,2'-azino-bis-(3-ethylbenzothiazoline-6-sulfonic acid) di-ammonium salt is added to each washed well and incubated for 15 minutes at room temperature. Then, a 100 μl of 1.5% oxalic acid is added to each well in order to terminate the enzyme reaction. Color development is spectrophotometrically measured at 415 nm. The degree of the color development is positively correlated with the amount of the antibody in the serum sample. An absorbance of each serum sample is obtained by subtracting an absorbance of the control well from that of the corresponding antigen-coated well.

The above serodiagnosis method is carried out with sera from healthy individuals, patients with benign disorders and patients with cancers.

The comparison of the absorbances determined for the above samples has shown that the serum samples of lung cancer patients have significantly higher absorbances than those of the patients with lung benign disorders as well as the healthy individuals. Furthermore, the serum samples of the patients with ovary cancer, larynx cancer, uterine cancer and liver cancer also show high levels in absorbance, indicating a significant difference in absorbance between these cancer samples and those of the healthy individuals.

The present invention will be now described more in detail referring to the following non-limiting Examples.

EXAMPLE 1

Acetone powder of porcine pancreas obtained according to a conventional method (J. Biol. Chem., 223, 457 (1956)) or crude trypsin powder (1:250, Difco) may be used as starting materials for the purification of the animal antigenic materials. The powder was suspended in A buffer (10 mM Tris-HCl, pH 7.4). The resulting suspension was centrifuged for 20 minutes at 10,000×g at 4° C. to obtain a supernatant (Supernatant-I). The precipitate was re-suspended in A buffer by stirring for 10 minutes at 4° C followed by the same centrifugation as described above to obtain a supernatant (Supernatant-II). The same procedures were repeated to obtain a supernatant (Supernatant-III). Supernatants-I, -II and -III thus obtained were mixed together and diluted with A buffer to a final concentration of 10 mg/ml.

The resulting solution was applied to Mono Q column (Pharmacia) previously equilibrated with A buffer in a ratio of 5 mg protein per 1 ml of the resin and washed with 5 column volumes of A buffer. After further washing with A buffer containing 150 mM NaCl, elution with a linear gradient of 150–350 mM NaCl was carried out and two materials, which may strongly react with the monoclonal antibody produced by HB4C5, were eluted at 260 mM and 300 mM NaCl, respectively. These materials are designated as Antigens-I and -II, respectively. On the SDS-PAGE described supra, both Antigens-I and -II migrated in each single band, indicating that their molecular weights are about 42,000 and 40,000, respectively. Consequently, Antigens-I and -II thus purified were deemed to have a high purity. Considering that the molecular weight of porcine trypsin is 23,000, it may be believed that these antigens are completely different from porcine trypsin which is abundant in porcine pancreas.

The results obtained in the above SDS-PAGE are shown below:

| | M.W. | Migration Distance | Rf |
|---|---|---|---|
| Bromophenol blue (dye marker) Markers (BIO-RAD) | 0.67K | 51.0 mm | 1 |
| Lysozyme | 14.4 | 50.5 | 0.99 |
| Trypsin Inhibitor | 21.5 | 48.5 | 0.95 |
| Carbonic Anhydrase | 31.0 | 43.5 | 0.85 |
| Ovalbumin | 45.0 | 37.5 | 0.74 |
| Bovine Serum Albumin | 66.2 | 33.0 | 0.65 |
| Phosphorylase B | 92.5 | 25.5 | 0.50 |
| Antigen-I | 42 | 39.3 | 0.771 |

| | M.W. | Migration Distance | Rf |
|---|---|---|---|
| | | -continued | |
| Antigen-II | 40 | 40.0 | 0.784 |

EXAMPLE 2

To identify the antigenic materials purified in EXAMPLE 1, they were compared with various carboxypeptidases as follows:

I. Comparison in an enzymatic activity:

According to the method described in Anal. Biochem., 171, 294 (1988), hydrolysis activity using hippuryl-L-phenylalanine as an enzyme substrate was determined spectrophotometrically at 254 nm. Bovine carboxypeptidase A (CPase A) used in this experiment is commercially available one (Sigma, No. C-0261 Type I, derived form bovine pancreas). The results are shown below:

| Sample | Concentration ($\mu$g/ml) | Activity ($OD_{254}$) |
|---|---|---|
| Procine-derived: | | |
| Antigen-I | 50 | 0.05 |
| Antigen-II | 50 | 0.06 |
| Bovine CPase A | 50 | 0.05 |

The above results clearly show that both Antigens-I and -II possess substantially the same CPase A activity as the commercial bovine CPase A.

II. Comparison in an immunological reactivity:

Rabbit antisera against Antigens-I and -II were prepared and employed in the enzyme immuno assay used in the above serodiagnosis method in order to determine their reactivities with the bovine CPase A and commercially available porcine carboxypeptidase B (CPase B, Sigma, No. C-7011 Type I, derived from porcine pancreas) as well as Antigens-I and -II. The results are shown below:

| | Reactivity ($OD_{415}$) | |
|---|---|---|
| Sample | Anti-Antigen-I Serum (diluted 1:1,000) | Anti-Antigen-II Serum (diluted 1:1,000) |
| Antigen | | |
| I | 0.899 | 0.772 |
| II | 0.836 | 0.843 |
| Bovine CPase A | 0.378 | 0.484 |
| Porcine CPase B | 0.027 | 0.015 |

As seen from the above results showing that the rabbit anti-Antigen-I serum may react with Antigen-II and the bovine CPase A as well as its immunogen Antigen-I, it may be considered that these materials are similar very well to each other. The rabbit anti-Antigen-II serum reacted in the same way. On the other hand, these antisera did not react with porcine CPase B, indicating a high specificity of these antisera to CPase A.

III. Comparison in amino acids sequence:

The amino acids sequence from at +3 to +13 of Antigen-II was determined as Ala-Thr-Tyr-His-Thr-Leu-Glu-Glu-Ile-Tyr, which is the same as the bovine CPase A except that Glu at +9 is replaced by Asp in the bovine Cpase A.

Furthermore, almost the same reaction patterns for samples were obtained in the serodiagnosis methods employing Antigens-I and -II and the bovine CPase A as an antigen, which will be shown in TABLE 3 in EXAMPLE 4 infra.

Based on the results shown above, porcine-derived Antigens-I and -II may be identified carboxypeptidase A.

EXAMPLE 3

An amount of antibodies of types IgG and IgM which reacted with Antigen-II, i.e., porcine CPase A as the antigen in sera of healthy individuals and patients with lung cancer was determined by the present serodiagnosis method as described supra.

TABLE 1

| Serum of Healthy Individuals | Reactivity ($OD_{415}$) | |
|---|---|---|
| | IgM | IgG |
| A | −0.084 | 0.073 |
| B | −0.065 | 0.046 |
| C | −0.088 | −0.156 |
| D | −0.169 | −0.010 |
| E | −0.061 | 0.022 |
| F | −0.072 | −0.030 |
| G | −0.001 | 0.035 |
| H | −0.010 | −0.030 |
| I | −0.128 | −0.026 |

TABLE 2

| Serum of Lung Cancer Patients | Reactivity ($OD_{415}$) | |
|---|---|---|
| | IgM | IgG |
| a | 0.770 | 0.184 |
| b | 0.122 | 0.083 |
| c | −0.018 | 0.539 |
| d | −0.004 | 0.225 |
| e | −0.037 | 0.420 |
| f | 0.010 | 0.033 |

As shown in TABLE 1, the levels in $OD_{415}$ of healthy individuals indicate around zero. Accordingly, if samples having the optical density at 415 nm of more than 0.1 were assumed to be positive, 2 IgM samples and 4 IgG samples out of the serum samples of 6 lung cancer patients were judged positive, showing that 5 sera of the lung cancer patients were positive in total.

The following EXAMPLEs were performed with respect to only IgG samples which showed higher positive ratios than IgM, which, however, never means that IgM is unnecessary for the serodiagnosis method.

EXAMPLE 4

By using Antign-II, the bovine CPase A, the porcine CPase B and mouse CPase A which was purified in the same method as in EXAMPLE 1, the serodiagnosis method according to the present invention was carried out to determine an amount of antibodies of type IgG in sera of healthy individuals, lung cancer patients and ovary cancer patients as well as to determine the reactivity of these materials with the human monoclonal antibody (MoAb) produced by HB4C5. These results obtained are summarized in TABLE 3.

It may be clearly shown from TABLE 3 that the serodiagnosis method according to the present invention, which employs the antigen recognized by the human monoclonal antibody, especially, carboxypeptidases such as CPase A and CPase B, may generally provide a satisfactory means for the detection of cancers.

TABLE 3

| Serum | | Reactivity (OD$_{415}$) | | | |
|---|---|---|---|---|---|
| | | Porcine CPase A | Porcine CPase B | Bovine CPase A | Mouse CPase A |
| 10% FCS/PBS | | 0.041 | 0.017 | 0.055 | 0.017 |
| 10 μg/ml MoAb | | 1.196 | 0.854 | 1.428 | 0.876 |
| Healthy | 1. | 0.116 | 0.017 | 0.113 | 0.007 |
| Individuals | 2. | 0.051 | 0.000 | 0.120 | 0.003 |
| | 3. | 0.091 | 0.005 | 0.125 | 0.008 |
| Lung Cancer | 1. | 0.393 | 0.111 | 0.428 | 0.211 |
| Patients | 2. | 0.866 | 0.356 | 0.802 | 0.565 |
| Ovary Cancer | 1. | 0.829 | 0.029 | 0.663 | 0.729 |
| Patients | 2. | 0.493 | 0.220 | 0.564 | 0.402 |
| | 3. | 0.404 | 0.199 | 0.553 | 0.303 |

EXAMPLE 5

The serodiagnosis method according to the present invention was carried out by using serum samples from patients with a various kinds of cancers including lung cancer, patients with benign disorders and healthy individuals and by employing the bovine CPase A as the antigen. The results are shown in FIG. 1. The serum samples of the healthy individuals and patients with benign disorders showed generally low reactivities, while many serum samples of the patients with cancers such as lung cancer, ovary cancer, larynx cancer, uterine cancer and liver cancer showed high reactivities in the serodiagnosis method. It is believed therefore that these results may prove a great usefulness of the serodiagnosis method of the present invention for the detection of cancers.

The positive ratio of each sample group was calculated based on the results in FIG. 1, in which an average OD$_{415}$ value of the healthy individuals was added to the value of 2 x S.D. (standard deviation), i.e., 0.28 and the resulting value was used as criterion for judging samples positive or not. The results are shown in TABLE 4 below.

TABLE 4

| Serum | Sample Number | Positive Sample Number | Positive Ratio (%) |
|---|---|---|---|
| 1. Healthy Individuals | 38 | 1 | 3 |
| 2. Lung Ca. | 26 | 14 | 54 |
| 3. Ovary Ca. | 14 | 10 | 71 |
| 4. Larynx Ca. | 4 | 4 | 100 |
| 5. Uterine Ca. | 5 | 3 | 60 |
| 6. Liver Ca. | 13 | 7 | 54 |
| 7. Rectum Ca. | 13 | 5 | 38 |
| 8. Stomach Ca. | 22 | 7 | 32 |
| 9. Gallbladder Ca. | 4 | 2 | 50 |
| 10. Pancreas Ca. | 6 | 0 | 0 |
| Benign Disorders | | | |
| 11. Lung | 14 | 0 | 0 |
| 12. Ovary | 5 | 0 | 0 |
| 13. Liver | 23 | 2 | 9 |
| 14. Gallbladder | 9 | 0 | 0 |
| 15. Pancreas | 5 | 0 | 0 |
| 16. Blood vas. | 4 | 0 | 0 |

As shown in the above results, the serum samples from the patients with lung cancer, ovary cancer, larynx cancer, uterine cancer and liver cancer show the positive ratios of more than 50%. On the other hand, the serum samples of pancreas cancer patients as well as of the healthy individuals and the patients with benign disorders show much lower positive ratios.

Accordingly, the present serodiagnosis method employing the antigen recognizable by the human monoclonal antibody produced by human-human hybridomas such as HB4C5 and derived from animals other than human, especially carboxypeptidase A, may be advantageously used for the detection of cancers such as lung cancer, ovary cancer, larynx cancer, uterine cancer and liver cancer.

What is claimed is:

1. A serological method for the detection of cancer, which comprises the steps of:
   (1) incubating a serum sample in a first incubation with an immobilized animal carboxypeptidase antigen recognized by the monoclonal antibody produced by hybridoma HB4C5 designated FERM BP-1879.
   (2) washing out antibodies in the serum sample, which are not bound to the antigen;
   (3) adding a labelled anti-human IgG or IgM for a second incubation;
   (4) washing out the labelled anti-human IgG or IgM not bound to the antibodies; and thereafter
   (5) detecting the amount of the labelled anti-human IgG or IgM bound to the antibodies as a measure of the presence of cancer.

2. The serological method according to claim 1, in which the cancer is lung cancer, ovary cancer, larynx cancer, uterine cancer, liver cancer, rectum cancer, or stomach cancer.

3. The serological method according to claim 1 or 2, in which the carboxypeptidase is carboxypeptidase A.

4. The serological method according to claim 1 or 2, in which the carboxypeptidase is carboxypeptidase B.

5. The serological method according to claim 3, in which the animal is swine, bovine or mouse.

6. The serological method according to claim 4, in which the animal is swine, bovine or mouse.

7. The serological method according to claim 3, wherein said labelled anti-human IgG or IgM is an enzyme-conjugated anti-human IgG or IgM.

8. The serological method according to claim 7, in which the enzyme is peroxidase.

9. A method for the determination of antibodies which bind to an animal carboxypeptidase antigen recognized by the monoclonal antibody produced by hybridoma HB4C5, designated FERM BP-1879 which comprises the steps of:
   (1) incubating a serum sample in a first incubation with an immobilized animal carboxypeptidase antigen recognized by the monoclonal antibody produced by hybridoma HB4C5;
   (2) washing out antibodies in the serum sample, which are not bound to the antigen;
   (3) adding a labelled anti-human IgG or IgM for a second incubation;
   (4) washing out the labelled anti-human IgG or IgM not bound to the antibodies; and thereafter
   (5) detecting the amount of the labelled anti-human IgG or IgM bound to the antibodies.

10. The method according to claim 9, in which the carboxypeptidase is carboxypeptidase A.

11. The method according to claim 9, in which the carboxypeptidase is carboxypeptidase B.

12. The method according to claim 9, 10 or 11, in which the animal is swine, bovine or mouse.

13. The method according to claim 12, wherein said labelled anti-human IgG or IgM is an enzyme-conjugated anti-human IgG or IgM.

14. The method according to claim 13, in which the enzyme is peroxidase.

* * * * *